US004001788B2

United States Statutory Invention Registration [19]

[11] Reg. Number: H1788

[45] Published: Feb. 2, 1999

Christon et al.

[54] MULTI-LAYER ABSORBENT PRODUCT WITH PEEL AWAY COMPONENTS

[76] Inventors: Patricia Lee Christon; Nicholas Albert Ahr, both of The Procter & Gamble Company, Winton Hill Technical Center, 6100 Center Hill Ave., Cincinnati, Ohio 45224

[21] Appl. No.: 527,166

[22] Filed: Sep. 12, 1995

[51] Int. Cl.[6] ..... A61F 13/00

[52] U.S. Cl. ..... 604/385.1

[58] Field of Search ..... 604/378, 389, 604/385.1, 386, 390, 387, 396

[56] References Cited

U.S. PATENT DOCUMENTS

| | | | |
|---|---|---|---|
| 2,929,379 | 3/1960 | Poulsen | 128/290 |
| 3,367,334 | 2/1968 | Testa | 128/290 |
| 3,580,252 | 5/1971 | Delort | 128/290 |
| 4,094,316 | 6/1978 | Nathanson | 128/156 |
| 4,097,943 | 7/1978 | O'Connell | 5/335 |
| 4,161,176 | 7/1979 | Harris, II et al. | 128/155 |
| 4,405,310 | 9/1983 | Karami | 604/383 |
| 4,425,130 | 1/1984 | Des Marais | 604/389 |
| 4,505,707 | 3/1985 | Feeney | 604/393 |
| 4,576,597 | 3/1986 | Hlaban | 604/390 |
| 4,605,404 | 8/1986 | Sneider | 604/385 |
| 4,657,538 | 4/1987 | Becker et al. | 604/381 |
| 4,765,477 | 8/1988 | Froidh et al. | 604/378 |
| 4,806,411 | 2/1989 | Mattingly, III et al. | 428/139 |
| 4,848,572 | 7/1989 | Herrera | 604/386 |
| 4,938,756 | 7/1990 | Salek | 604/378 |
| 4,964,857 | 10/1990 | Osborn | 604/395 |
| 5,057,096 | 10/1991 | Faglione | 604/385.1 |
| 5,087,254 | 2/1992 | Davis et al. | 604/385.1 |
| 5,429,631 | 7/1995 | Grenier | 604/385.1 |
| 5,458,591 | 10/1995 | Roessler et al. | 604/385.1 |

FOREIGN PATENT DOCUMENTS

| | | | |
|---|---|---|---|
| 406121812 | 5/1994 | Japan . | |
| 9321878 | 11/1993 | WIPO . | |
| WO 95/29655 | 11/1995 | WIPO | A61F 13/15 |

*Primary Examiner*—Charles T. Jordan
*Assistant Examiner*—Meena Chelliah

[57] ABSTRACT

The present invention provides an absorbent article which includes a first absorbent article and a second absorbent article releasably secured to one another. The first absorbent article includes a grasping member having a portion that extends outwardly from the periphery of the first absorbent article. The grasping member is used to separate the first absorbent article from the second absorbent article after the first absorbent article has become soiled.

11 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

MULTI-LAYER ABSORBENT PRODUCT WITH PEEL AWAY COMPONENTS

FIELD OF THE INVENTION

The present invention relates to absorbent articles such as incontinence pads, sanitary napkins, pantiliners, and the like, and more particularly to absorbent articles having a first absorbent article and a second absorbent article releasably secured to one another.

BACKGROUND OF THE INVENTION

Various absorbent articles such as sanitary napkins and light to medium incontinent devices exist which absorb body exudates such as menses, urine and fecal matter. Disposable products of this type generally comprise fluid permeable topsheet material, fluid absorbent core, and fluid impermeable backsheet material. Various shapes, sizes and thicknesses of such article have been explored in an attempt to make their use more comfortable and convenient. For example, U.S. Pat. No. 5,389,094, Lavash et al., issued Feb. 14, 1995, U.S. Pat. No. 5,383,869, Osborn, III, issued Jan. 24, 1995, U.S. Pat. No. 5,382,245, Thompson et al., issued Jan. 17, 1995 and U.S. Pat. No. 5,346,486, Osborn III, et al. issued Sep. 13, 1994 show numerous shapes, sizes, thicknesses and other alternate variations.

There may be times when a user's needs may be variable or uncertain. At those times, a user may initially employ a first absorbent article, but may need to carry additional absorbent articles in reserve. Such is not always convenient, however. It would be desirable, then, for a user to be able to readily employ a second absorbent article after the first absorbent article has become soiled without having to retrieve the second absorbent article from reserve.

SUMMARY OF THE INVENTION

The present invention provides an absorbent article comprising a first absorbent article and a second absorbent article releasably secured to one another. Each absorbent article includes a periphery comprising a pair of end edges and a pair of longitudinal edges, a body facing surface and a garment facing surface. The first and second absorbent articles comprise a liquid previous topsheet, a liquid impervious backsheet joined to the topsheet, and an absorbent core positioned the topsheet and backsheet.

The second absorbent article may have similar or different geometric dimensions as the first absorbent article, and is positioned beneath the garment facing surface of the first absorbent article. The first and second absorbent articles may have similar or different absorptive capacities.

The absorbent article includes releasable securement means for releasably securing the first and second absorbent articles together. At least one grasping member is disposed on at least the first absorbent article. The grasping member comprises a tab having a fixed portion joined to the first absorbent article and an extended portion extending outwardly from the periphery of the first absorbent article. Preferably, the second absorbent article will also include at least one grasping member comprising a tab having a fixed portion joined to the second absorbent article and an extended portion extending outwardly from the periphery of the second absorbent article.

In a preferred embodiment, the grasping member comprises disposal means positioned on the first surface of the extended portion with a release liner thereon to cover and protect the disposal means prior to use; e.g., protecting an adhesive layer from premature exposure to the air.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composed or otherwise disposed of in an environmentally compatible manner). As used herein, the term "sanitary napkin" or "napkin" refers to devices which absorb and contain body exudates, and more specifically, refers to an absorbent article which is worn by females adjacent to the pudendal region, generally external to the urogenital region, and which is intended to absorb and contain menstrual fluids and other vaginal discharges from the wearer's body (e.g., blood, menses, and urine). As used herein, the term "pudendal" refers to the externally visible female genitalia. It should be understood, however, that the present invention is also applicable to other feminine hygiene garments or catamenial pads such as pantiliners or other absorbent articles such as incontinence pads, and the like.

Figure 1:
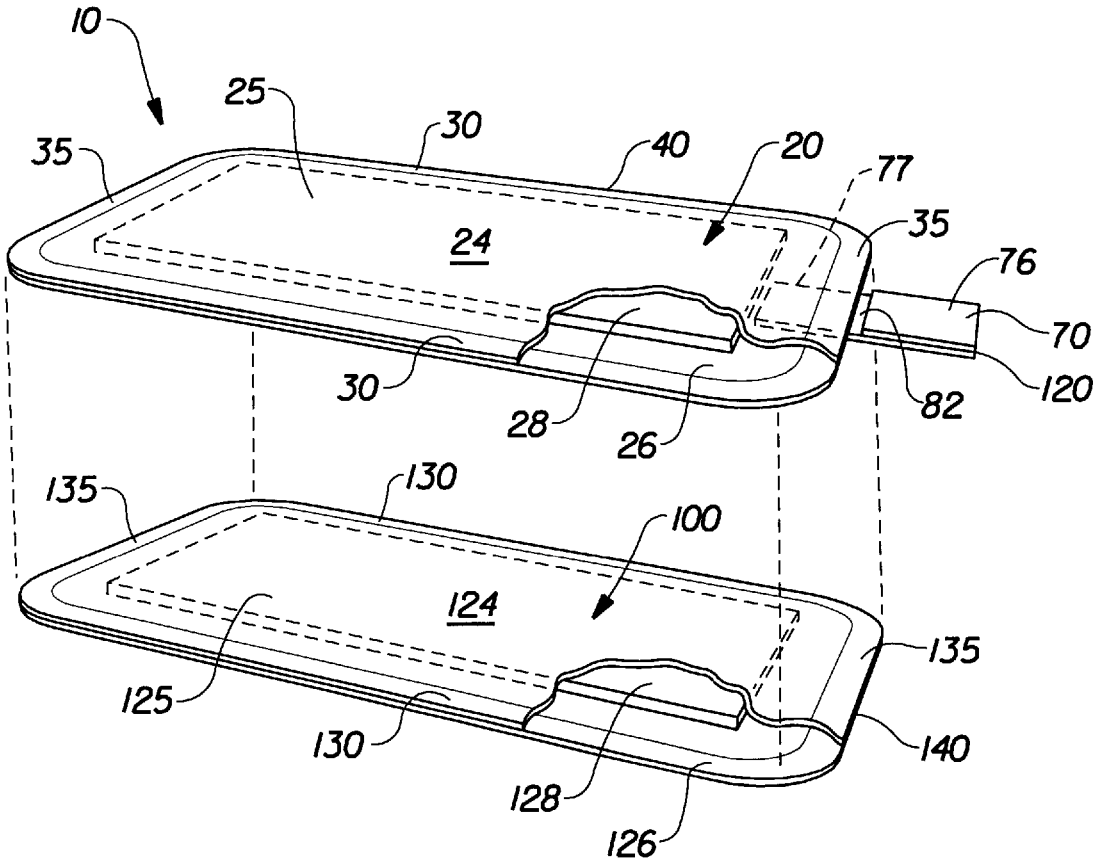
FIG. 1 is an exploded perspective view of the absorbent article of the present invention having portions cut away to reveal underlying structure.

FIG. 1 is an exploded perspective view of an absorbent article 10 of the present invention. The absorbent article 10 comprises a first absorbent article 20 and a second absorbent article 100. In the embodiment shown in FIG. 1, the first absorbent article 20 and the second absorbent article 100 have the same width and length dimensions.

The first absorbent article 20 is shown in FIG. 1 with portions of the structure being cut-away to more clearly show the construction of the first absorbent article 20. The first absorbent article 20 preferably comprises a liquid previous topsheet 24, a liquid impervious backsheet 26 joined with the topsheet 24, and an absorbent core 28 positioned between the topsheet 24 and the backsheet 26.

The first absorbent article 20 has two surfaces, a body-contacting surface or "body surface" 25 and a garment surface 27 (not shown). The body surface 25 is intended to be worn adjacent to the body of the wearer while the garment surface 27 is on the opposite side and is intended to be placed adjacent to the second absorbent article 100. FIG. 1 also shows that the first absorbent article 20 has a periphery 40 which comprises the longitudinal edges 30 and the end edges 35.

While the topsheet, the backsheet, and the absorbent core may be assembled in a variety of well known absorbent article configurations (including so called "tube" products or side flap products), preferred absorbent article configurations are described generally in U.S. Pat. No. 4,950,264, "Thin, Flexible Sanitary Napkin" issued to Osborn on Aug. 21, 1990; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987. Each of these patents are hereby incorporated herein by reference. FIG. 1 shows a preferred embodiment of the first absorbent article 20 in which the topsheet 24 and the backsheet 26 have length and width dimensions generally larger than those of the absorbent core 28. The topsheet 24 and the backsheet 26 extend beyond the edges of the absorbent core 28 to form portions of the periphery 40.

The absorbent core 28 may be any absorbent means which is capable of absorbing or retaining liquids (e.g., menses and/or urine). As shown in FIG. 1 the absorbent core 28 has a body surface, a garment surface, side edges, and end edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core 28 may also be varied (e.g., the absorbent core 28 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 28 should, however, be compatible with the design loading and the intended use of the first absorbent article 20. Further, the size and absorbent capacity of the absorbent core 28 may be varied to accommodate different uses such as incontinence pads, pantiliners, regular sanitary napkins, or overnight sanitary napkins.

Exemplary absorbent structures for use as the absorbent core 28 of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 26 and the topsheet 24 are positioned adjacent the garment surface and the body surface, respectively, of the absorbent core 28 and are preferably joined thereto and to each other by attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds; dynamic mechanical bonds, or any other suitable attachment means or combinations of these attachment means as are known in the art.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the absorbent articles described herein such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 26 may permit vapors to escape from the absorbent core 28 (i.e., breathable) while still preventing exudates from passing through the backsheet 26.

The topsheet 24 is compliant, soft feeling, and non-irritating to the wearer's skin. Further, the topsheet 24 is liquid previous permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S.

Pat. No. 3,929,135, entitled. "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the is formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

The second absorbent article 100 preferably comprises a liquid pervious topsheet 124, a liquid impervious backsheet 126 secured to the topsheet 24, and an absorbent core 128 positioned between the topsheet 124 and the backsheet 126.

The second absorbent article 100 has two surfaces, an absorbent article-contacting surface 125 which becomes a "body surface" at the removal of the first absorbent article 20 and a garment surface 127 (not shown). The second absorbent article 100 is shown in FIG. 1 with portions of the structure being cut-away to more clearly show the construction of the second absorbent article 100. The absorbent article-contacting surface is intended to be worn adjacent to the outer surface 27 of the backsheet 26 of the first absorbent structure 20. Upon removal of the first absorbent article 20 from a wearer's undergarment, the absorbent article-contacting surface of the second absorbent structure 100 will become the body-contacting surface 125 and will thus be worn adjacent to the wearer's body. FIG. 1 also shows that the second absorbent article 100 has a periphery 140 which comprises longitudinal edges 130 and end edges 135.

While the topsheet, the backsheet, and the absorbent core may be assembled in a variety of well known absorbent article configurations (including so called "tube" products or side flap products), preferred absorbent article configurations are described generally in U.S. Pat. No. 4,950,264, "Thin, Flexible Sanitary Napkin" issued to Osborn on Aug. 21, 1990; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987. Each of these patents are hereby incorporated herein by reference. FIG. 1 shows a preferred embodiment of the second absorbent article 100 in which the topsheet 124 and the backsheet 126 have length and width dimensions generally larger than those of the absorbent core 128. The topsheet 124 and the backsheet 126 extend beyond the edges of the absorbent core 128 to form portions of the periphery 140.

The absorbent core 128 may be any absorbent means which is capable of absorbing or retaining liquids (e.g., menses and/or urine). As shown in FIG. 1 the absorbent core 28 has a body surface, a garment surface, side edges, and end edges. The absorbent core 128 may be manufactured in a wide variety of sizes and shapes (e.g., rectangular, oval, hourglass, dog bone, asymmetric, etc.) and from a wide variety of liquid-absorbent materials commonly used in various absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core 128 may also be varied (e.g., the absorbent core 128 may have varying caliper zones (e.g., profiled so as to be thicker in the center),. hydrophilic gradients, superabsorbent gradients, or lower density and lower average basis weight acquisition zones; or may comprise one or more layers or structures). The total absorbent capacity of the absorbent core 128 should, however, be compatible with the design loading and the intended use of the second absorbent article 100. Further, the size and absorbent capacity of the absorbent core 128 may be varied to accommodate different uses such as incontinence pads, pantiliners, regular sanitary napkins, or overnight sanitary napkins. The absorbent capacity of the absorbent core 128 may be the same as, greater than, or less than the absorbent capacity of the absorbent core 28 of the first absorbent article 20.

Exemplary absorbent structures for use as the absorbent core 128 of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 126 and the topsheet 124 are positioned adjacent the garment surface and the body surface, respectively, of the absorbent core 128 and are preferably joined thereto and to each other by attachment means (not shown) such as those well known in the art. For example, the backsheet 126 and/or the topsheet 124 may be secured to the absorbent core 128 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague,. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 126 is impervious to liquids (e.g., menses and/or urine) and is preferably manufactured from a thin plastic film, although other flexible liquid impervious materials may also be used. The backsheet 126 prevents the exudates absorbed and contained in the absorbent core 128 from wetting articles which contact the second absorbent article 100 such as pants, pajamas and undergarments. The backsheet 126 may thus comprise a woven or nonwoven material, polymeric films such as thermoplastic films of polyethylene or polypropylene, or composite materials such as a film-coated nonwoven material. Preferably, the backsheet 126 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP39385. The backsheet 126 is preferably embossed and/or matte finished to provide a more clothlike appearance. Further, the backsheet 126 may permit vapors to escape from the absorbent core 128 (i.e., breathable) while still preventing exudates from passing through the backsheet 126.

The topsheet 124 is compliant, soft feeling, and non-irritating to the wearer's skin. Further, the topsheet 124 is liquid pervious permitting liquids (e.g., menses and/or urine) to readily penetrate through its thickness. A suitable topsheet 124 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet 124 comprises an apertured formed film. Apertured formed films are preferred for the topsheet 124 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in the preceding section First Absorbent Article Structure and each of these patents are incorporated herein by reference. The preferred topsheet for the present invention is the formed film described in one or more of the above patents and marketed on sanitary napkins by The Procter & Gamble Company of Cincinnati, Ohio as "DRIWEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et. al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

In a preferred embodiment of the present invention, an acquisition layer(s) may be positioned between the topsheets and the absorbent cores of the first-absorbent article 20 and the second absorbent article 100, respectively. An acquisition layer may serve several functions including improving wicking of exudates over and into the absorbent core. There are several reasons why the improved wicking of exudates is important, including providing a more even distribution of the exudates throughout an absorbent core and allowing an absorbent article described herein to be made relatively thin. (The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of absorbent articles disclosed herein having an acquisition layer and a topsheet are more fully described in U.S. Pat. No. 4,950,264 issued to Osborn and U.S. patent application Ser. No. 07/944,764, "Absorbent Article Having Fused Layers", filed Oct. 7, 1992, in the names of Cree, et al. Each of these references are incorporated herein by reference. In a preferred embodiment, the acquisition layer may be joined with the topsheet by any of the conventional means for joining webs together, most preferably by fusion bonds as is more fully described in the above-referenced Cree application.

The articles are releasably secured to another such that after the first absorbent article has been soiled, it may be separated from the second absorbent article, leaving the second absorbent article in place in the user's panties. The releasable securement means, preferably located on the peripheries 40 and 140 of the first and second absorbent articles 20 and 100, respectively may comprise any releasable securement means known in the art to be compatible with backsheet, topsheet and absorbent core materials. However, releasable securement means must be chosen that will join the desired portion or portions of the first absorbent article 20 with the desired portion or portions of the second absorbent article 100 while not joining those portions of the first absorbent article 20 and the second absorbent article 100 which have been designated to remain unsecured; e.g., only the peripheries 40 and 140 (longitudinal side edges 30 and 130 and end edges 35 and 135) of the first and second absorbent articles 20 and 100 are to be releasably secured together. Suitable releasable securement means may include, but are not limited to, adhesives, pressure bonding means, heat bonding means, heat and pressure bonding means, ultrasound bonding means, infrared bonding means, dynamic mechanical bonding means or any other disposal means or combination of releasable securement means known in the art. The most preferred releasable securement means for this invention is water-soluble adhesives such as Airflex 401 produced by Air Products & Chemicals, Incorporated, located in Allentown, Pa.

In use, the second absorbent article 100 can be held in place by any support means or attachment means 90 (not shown) well-known for such purposes. Preferably, the absorbent article 10, comprising the first absorbent article 20 and the second absorbent article 100 is placed in the user's undergarment or panty and secured thereto by a fastener located on the outer surface 127 of the backsheet 126 of the second absorbent article 100 such as an adhesive. The adhesive attachment means 90 provides a means for securing the second absorbent article 100 in the crotch portion of the panty. Thus, a portion or all of the outer surface 127 of the backsheet 126 comprises an adhesive attachment means 90. Any adhesive or glue used in the art for such purposes can be used for the adhesive attachment means 90 herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the second absorbent article 100 is placed in use, the pressure-sensitive adhesive attachment means 90 is typically covered with a removable release liner in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. In a preferred embodiment, the second absorbent article 100 of the present invention is used by removing the release liners 156 (not shown), and thereafter placing the second absorbent article 100 in a panty so that the adhesive attachment means 90 contacts the panty. As one function, the adhesive attachment means 90 maintains the second absorbent article 100 in its position within the panty during use.

Figure 3:
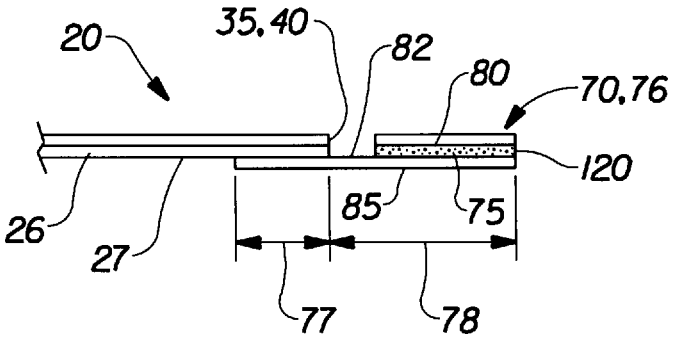
FIG. 3 is a fragmentary side view of the first absorbent article showing the grasping member.

As shown in FIGS. 1 and 3 the first absorbent article 20 includes a grasping member 70. Grasping member 70 preferably comprises a tab 76. The tab 76 has a first surface 82 facing the wearer and a second surface 85 facing the second absorbent article 100. The tab 76 is joined to the backsheet 26 to create a fixed portion 77 (i.e., that portion of the tab 76 joined to the first absorbent article 20 during manufacture). The tab 76 has another element which is the extended portion 78 which is that portion of the tab 76 which extends outwardly beyond the periphery 40 of the first absorbent article 20 and that is grasped by the user to separate the first absorbent article 20 from the second absorbent article 100. The distal end 120 of the tab 76 preferably has rounded corners to eliminate the possibility of harsh corner edges contacting the wearer's skin.

As shown in FIGS. 1 and 3 the tab 76 is joined to the first absorbent article 20 such that the extended portion 78 extends outwardly from an end edge 35 of the first absorbent article 20. Alternatively, the tab 76 may be joined to the first absorbent article 20 such that the extended portion 78 of the tab 76 extends outwardly from one of the longitudinal edges 30.

In the embodiment shown in FIG. 1, the fixed portion 77 is joined to the outer surface 27 of the backsheet 26. Alternatively, the fixed portion 77 may be joined to the first absorbent article 20 by positioning the fixed portion 77 between the topsheet 24 and the backsheet 26. While the fixed portion 77 may be joined directly to the body contacting surface 25 of the topsheet 24, this is not preferred as the tab 76 may interface with the fluid handling properties of the topsheet and may also be subjected to soiling. Also, but not preferably, the tab 76 may extend from the absorbent core 28 or at least may have its fixed portion 77 located between the topsheet 24 and backsheet 26, and thus extend outwardly therefrom; this configuration is also possible for the second absorbent article 100 as disclosed herein.

The tab 76 may also comprise a disposal means 75 joined to the first surface 82 of the extended portion 78 of tab 76. The disposal means 75 allows the first absorbent article 20 to be secured in a configuration that provides convenient disposal of the first absorbent article 20 and reduces leakage of liquid and/or solid exudates. Thus, the disposal means 75 may be any structure that allows the first absorbent article 20 to be folded or rolled up into a configuration for disposal and secured in that configuration. For example, the disposal means 75 may comprise a member of different elements positioned on the first surface 82 of the tab 76 such as an adhesive, or any other compatible element known to those of skill in the art. Compatible adhesives for the disposal means 75 can be, but are not limited to, Century Adhesives Corporation of Columbus, Ohio; and Instant Lock 34-2823 manufactured by the National Starch and Chemical Company of Bridgewater, NJ. Suitable adhesive fasteners are also described in U.S. Pat. No. 4,917,697. Release member 80 protects the adhesive disposal means 75 from drying out prior to use. A suitable release member is described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis.

After the first absorbent article 20 has been soiled, the user removes the absorbent article 20 from his/her undergarment via the grasping member 70. At removal, the absorbent article 20 is peeled or pulled away from the second absorbent article 100 preferably in a front (of user) to back (of user) motion. Upon removal of the absorbent article 20, the adhesive disposal means 75 is exposed. The adhesive disposal means 75 most preferably attaches to the backsheet 26 of the absorbent article 20 thus producing an absorbent article 20 that is folded at or near its lateral axis, or it is tri-folded along two axis parallel to the lateral axis, or is rolled in a circular configuration. The folded and sealed absorbent article 20 has its backsheet 26 as the exterior surface, and its topsheet 24 as the interior and soiled surface. The absorbent article 20 is now ready for disposal and remains sealed, and thereby at least partially reduces liquid, solid and vapor leakage.

A grasping member 70 will most preferably comprise polyethylene, but can alternatively comprise paper and/or cloth. Furthermore, the grasping member 70 can be an extension of the backsheet 26, topsheet 24 or core 28. In alternative embodiments the grasping member 70 can be positioned on the longitudinal edges 30 and 130 of the first and second absorbent articles 20 and 100, respectively. For an absorbent article which includes flaps, grasping members 70 can be placed on the flaps 54 and/or along the longitudinal edges 30. Disposal means 75 can be included on each of the grasping members 70.

In an alternative embodiment, the disposal means 75 is a mechanical loop or hook type as disclosed in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,846,815 entitled "Disposable Diaper Having an Improved Fastening Device" issued to Scripps on Jul. 11, 1989 and are incorporated herein by preference. For a hook disposal means 75, loops will on the backsheet and optimally placed to receive the hooks. For a loop disposal means 75, hooks will be on the backsheet and optimally placed to receive the loops.

Figure 2:
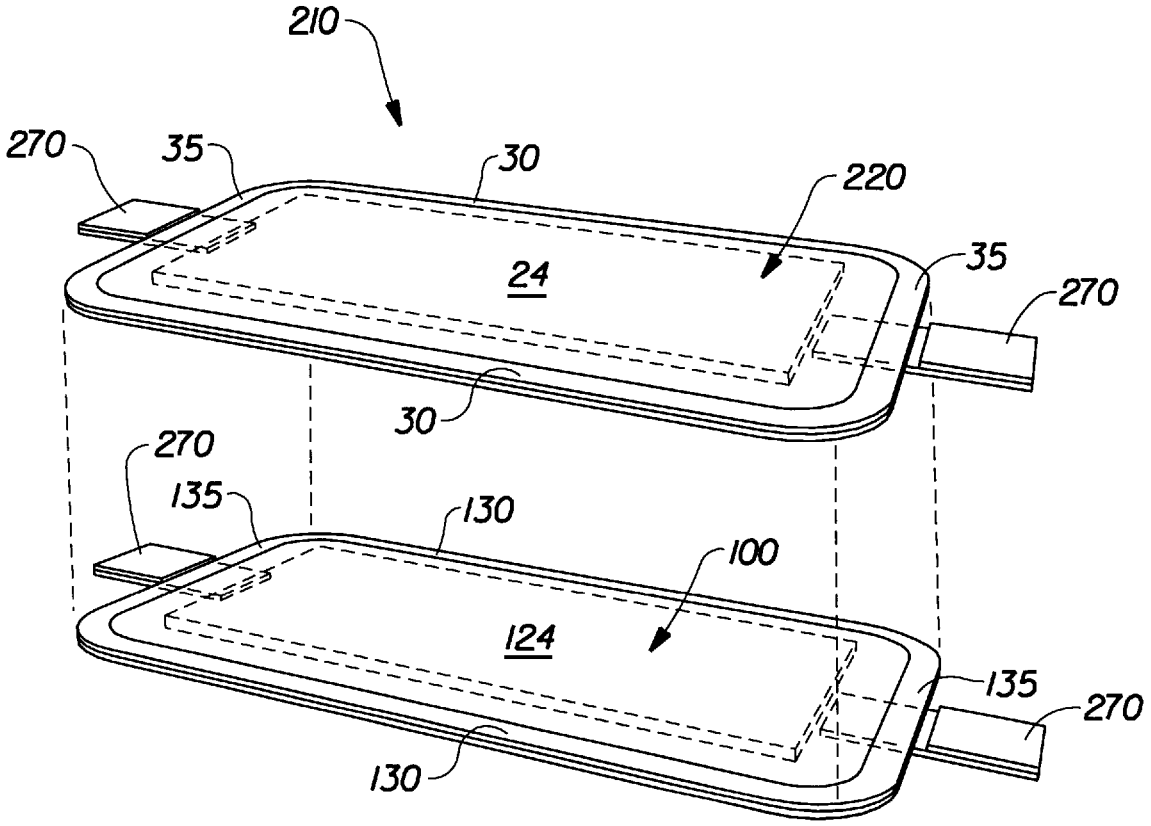
FIG. 2 is an exploded perspective view of another embodiment of the absorbent article of the present invention.

FIG. 2 discloses another embodiment of an absorbent article of the present invention. Absorbent article 210 comprises first absorbent article 220 and second is absorbent article 300. The absorbent articles 220 and 300 each comprise at least one, and preferably two grasping members 270. At least one grasping member 270 of each absorbent article 220 and 300, respectively, preferably includes disposal means covered by a release member 80 (not shown). Preferably, the disposal means is located on both grasping member of the first and second absorbent articles, respectively. As is shown, the tabs 76 are located along the side edges 30 of the absorbent articles 20 and 100.

In an alternative embodiment of the present invention, at least one of the absorbent articles described herein, can have two flaps, each of which are adjacent to and extend laterally from the longitudinal edges of the absorbent core. The flaps are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means, and preferably adhesive, on their garment surface so that the flaps can fold back under the panty and attach to the garment facing side of the panty or one flap to another. In this way, the flaps serve to keep the second absorbent article properly positioned in the panty. The flaps can be constructed of various materials including materials similar to the topsheet, backsheet, tissue, or combination of these materials. Further, the flaps may be a separate element attached to the main body of the first absorbent article and/or second absorbent article or can comprise extensions of their respective topsheets and backsheets (i.e., a unitary construction). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. Each of these patents are incorporated herein by reference.

The number of absorbent articles which can be used and releasably secured together ranges from 2 to 15, most preferably, the range is from 2 to 3. In a preferred embodiment, the first and second absorbent articles have the same dimensions, e.g., width, length, and thickness, and are positioned one-to-another such that the periphery along the outer surfaces of the backsheet of the first absorbent article is releasably secured to the periphery of the garment, article-contacting surface of the topsheet of the second absorbent article. For a third absorbent article (not shown), the periphery along the outer surface of the backsheet of the second absorbent article is releasably secured to the periphery of the garment facing surface of the topsheet of the third absorbent article. All subsequent absorbent articles will be releasably secured herein whereas a top, immediately preceding absorbent article and a subsequent, immediately following absorbent article will be releasably secured as described above with respect to the first and second absorbent articles 20 and 100.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

a first absorbent article having a periphery comprising a pair of end edges and a pair of longitudinal edges, a body facing surface and a garment facing surface, said first absorbent article comprising a liquid pervious topsheet, a liquid impervious backsheet joined to said topsheet, and an absorbent core positioned between said topsheet and said backsheet;

a second absorbent article having a periphery comprising a pair of end edges and a pair of longitudinal edges, a body facing surface and a garment facing surface, said second absorbent article comprising a liquid pervious topsheet, a liquid impervious backsheet joined to said topsheet, and an absorbent core positioned between said topsheet and said backsheet;

releasable securement means for releasably securing said first and second absorbent articles together, said first and second absorbent articles being releasably secured together at their peripheries; and at least one grasping member, disposed on at least said first absorbent article, comprising a tab having a fixed portion joined to said first absorbent article and an extended portion connected to said fixed portion and extending longitudinally outwardly from said end edge of said periphery of said first absorbent article, said extended portion comprising a first surface and a second surface.

2. The absorbent article of claim 1 further comprising disposal means joined to said first surface of said extended portion of said grasping member for allowing the first absorbent article to be secured in a configuration that provides convenient disposal of said first absorbent article.

3. The absorbent article of claim 2 wherein said disposal means comprises an adhesive layer.

4. The absorbent article of claim 3 further comprising a release member joined to said adhesive layer.

5. The absorbent article of claim 1 wherein said first absorbent article and said second absorbent article are releasably secured together by heat-sealing.

6. The absorbent article of claim 1 wherein said first absorbent article and said second absorbent article are releasably secured together by a water soluble adhesive.

7. The absorbent article of claim 1 wherein said backsheet of said second absorbent article comprises a panty fastening adhesive and a release liner joined to said panty fastening adhesive.

8. The absorbent article of claim 1 wherein at least said second absorbent article comprises at least two flaps disposed adjacent to and extending laterally outwardly from each said longitudinal edge, thereby having at least one of said flaps on each said longitudinal edge.

9. The absorbent article of claim 1 wherein said first and second absorbent articles are sanitary napkins.

10. The absorbent article of claim 1 wherein said first and second absorbent articles are incontinence pads.

11. The absorbent article of claim 1 wherein said first absorbent article is positioned above said second absorbent article such that said backsheet of said first absorbent article is adjacent to said topsheet of said second absorbent article.

* * * * *